United States Patent [19]

Vacca

[11] Patent Number: 5,373,684
[45] Date of Patent: Dec. 20, 1994

[54] PROCESS AND APPARATUS USED IN PRODUCING PREFILLED, STERILE DELIVERY DEVICES

[75] Inventor: Rita D. Vacca, Glendale, Mo.

[73] Assignee: Mallinckrodt Medical, Inc., St. Louis, Mo.

[21] Appl. No.: 988,265

[22] Filed: Dec. 14, 1992

[51] Int. Cl.⁵ .............................................. B65B 55/02
[52] U.S. Cl. ........................................ 53/425; 53/440; 53/471
[58] Field of Search ................. 53/425, 426, 440, 471, 53/467; 141/18, 25, 92; 206/365; 220/661; 222/388; 604/218, 236, 238

[56] References Cited

U.S. PATENT DOCUMENTS

| | | | |
|---|---|---|---|
| 1,665,564 | 4/1928 | Reitz | 604/218 X |
| 2,263,865 | 11/1941 | Bailen | 604/218 X |
| 2,443,981 | 6/1948 | Funk et al. | 141/18 X |
| 3,401,692 | 9/1968 | Harris, Jr. | 222/388 X |
| 3,814,941 | 6/1974 | Czaplinski | 604/218 X |
| 3,872,864 | 3/1975 | Allen, Jr. | |
| 4,273,263 | 6/1981 | Voegele et al. | |
| 4,323,066 | 4/1982 | Bourdon | |
| 4,718,463 | 1/1988 | Jurgens, Jr. et al. | 141/91 X |
| 4,772,273 | 9/1988 | Alchas | 604/218 |
| 4,838,866 | 6/1989 | Marshall, Sr. | 604/236 X |
| 4,842,581 | 6/1989 | Davis | 604/218 X |
| 4,902,421 | 2/1990 | Pascale et al. | 604/190 X |

Primary Examiner—John Sipos
Assistant Examiner—Daniel Moon
Attorney, Agent, or Firm—Rothwell, Figg, Ernst & Kurz

[57] ABSTRACT

A process and apparatus used in manufacturing prefilled, sterile delivery devices such as syringe assemblies. The process includes sealing a syringe container portion at both ends and filling the same through a port provided in the container portion between the two ends. After filling, the port is closed and sealed and the syringe assembly is sterilized to provide a sterile delivery device with sterile contents. A suitable syringe container portion for producing prefilled, sterile delivery devices is also disclosed.

12 Claims, 2 Drawing Sheets

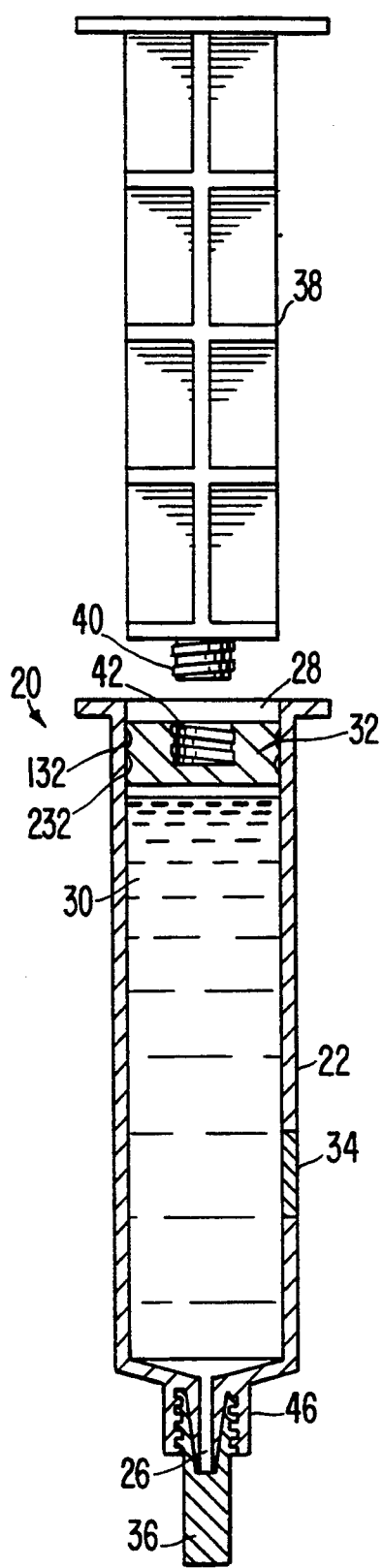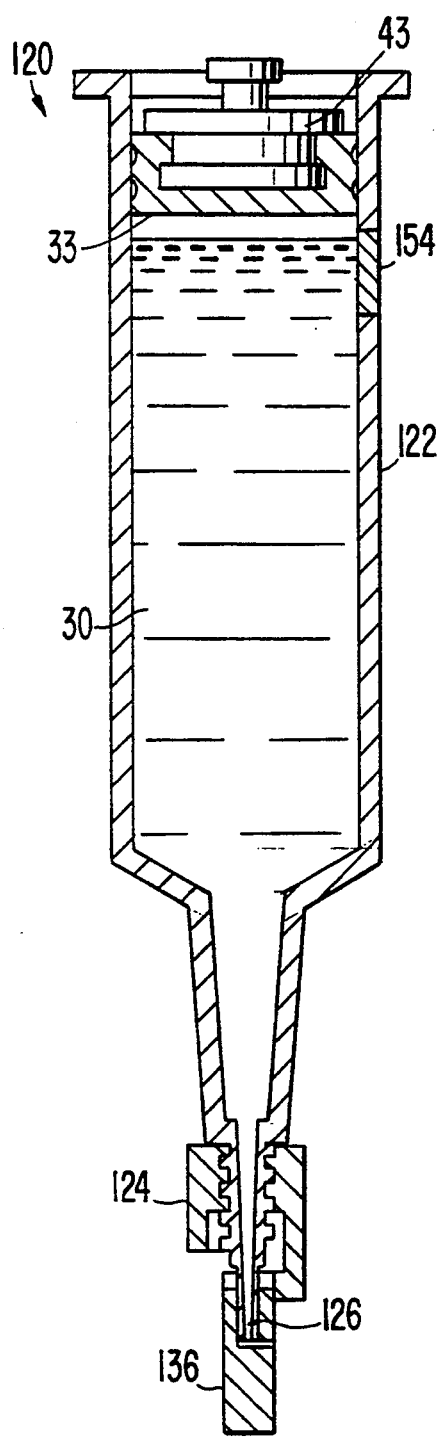

5,373,684

PROCESS AND APPARATUS USED IN PRODUCING PREFILLED, STERILE DELIVERY DEVICES

FIELD OF THE INVENTION

This invention relates to processes for producing prefilled, sterile delivery devices containing various media such as pharmaceutical fluids suitable for injection in vivo for use in the diagnosis and/or treatment of medical conditions.

DESCRIPTION OF THE PRIOR ART

It is known in the prior art to produce prefilled, sterile glass syringes in which the syringe parts are washed and sterilized prior to assembly, filling and sealing with a piston. The assembled and sealed syringes are then autoclaved to provide sterile syringes with sterile contents.

It is further known in the prior art to produce prefilled, sterile plastic syringes by first removing contaminants from the syringe barrel, the piston, and the tip seal, then placing the tip seal on the syringe nozzle, filling the syringe with liquid material, and then assembling the piston in the open end of the syringe barrel. The assembled syringes are then autoclaved to sterilize the syringes and their contents. Such techniques are disclosed in U.S. Pat. Nos. 4,628,969 and 4,718,463.

In carrying out the processes disclosed in the aforementioned patents, problems can arise from the placement or assembly of the tip seal and the piston on the syringe barrel. Specifically, the tip seal can be attached too loosely or too tightly, or it can be bent or misoriented on the syringe barrel. Additionally, the piston, which is assembled in the open end of the syringe barrel after filling of the same, is sometimes incorrectly placed in the barrel. Such incorrect placement or assembly of the tip seal and piston can prevent or adversely affect proper sealing of the syringe.

A significant problem that arises from an improper piston seal is bridging, i.e. the fluid contents, which should be completely contained within the barrel but below the bottom surface of the piston, flow past the piston bottom surface during assembly of the piston in the filled syringe barrel. The piston is often formed with a series of longitudinally spaced concentric seal rings or ridges extending outwardly from the side edge of the piston for engaging the interior wall of the barrel. The side edge of the piston has corresponding indentations disposed between adjacent seal rings. In a properly filled syringe, the fluid contents are contained within the barrel below the lowermost seal ring of the piston. However, when bridging occurs, a portion of the fluid contents passes this lowermost seal ring and becomes disposed within one of or several of the aforementioned indentations. This portion of the fluid serves as a pathway by which microbes or the like can pass from the non-sterile exterior of the syringe and piston to the sterile syringe contents.

Accordingly, it is an object of the present invention to provide a process for producing prefilled, sterile delivery apparatus in which the aforementioned problems are overcome.

SUMMARY OF THE INVENTION

The present invention provides a process for producing prefilled, sterile delivery apparatus in which proper placement of the piston and tip seal can be obtained and verified prior to filling the barrel portion of the apparatus with a desired quantity of fluid material.

Other features of the present invention will be apparent from the following description of the preferred embodiments taken in conjunction with the accompanying drawings wherein:

BRIEF DESCRIPTION OF THE DRAWINGS

FIG. 3 is a sectional view of the embodiment shown in FIG. 1 wherein the syringe barrel is filled and sealed.

FIG. 4 is a sectional view of the embodiment shown in FIG. 2 wherein the syringe barrel is filled and sealed.

DETAILED DESCRIPTION OF THE PREFERRED EMBODIMENTS

Figure 1:
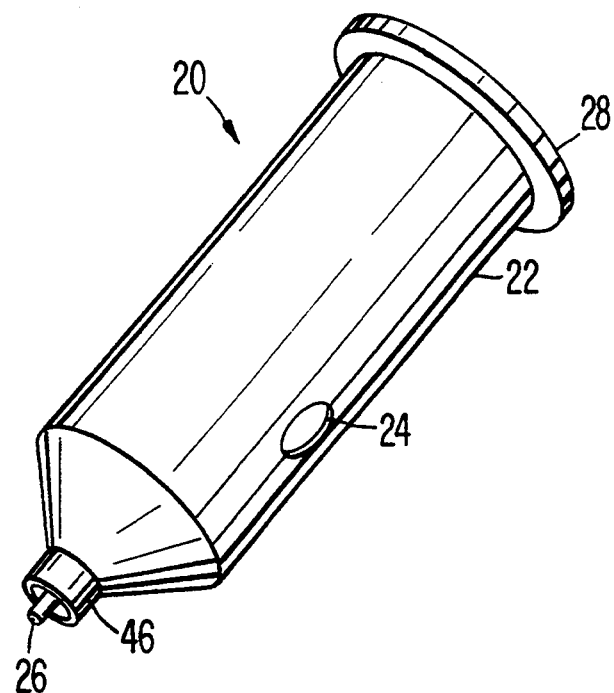
FIG. 1 is a perspective view of an empty syringe barrel used in producing a delivery apparatus according to a first embodiment of the present invention.
Figure 2:
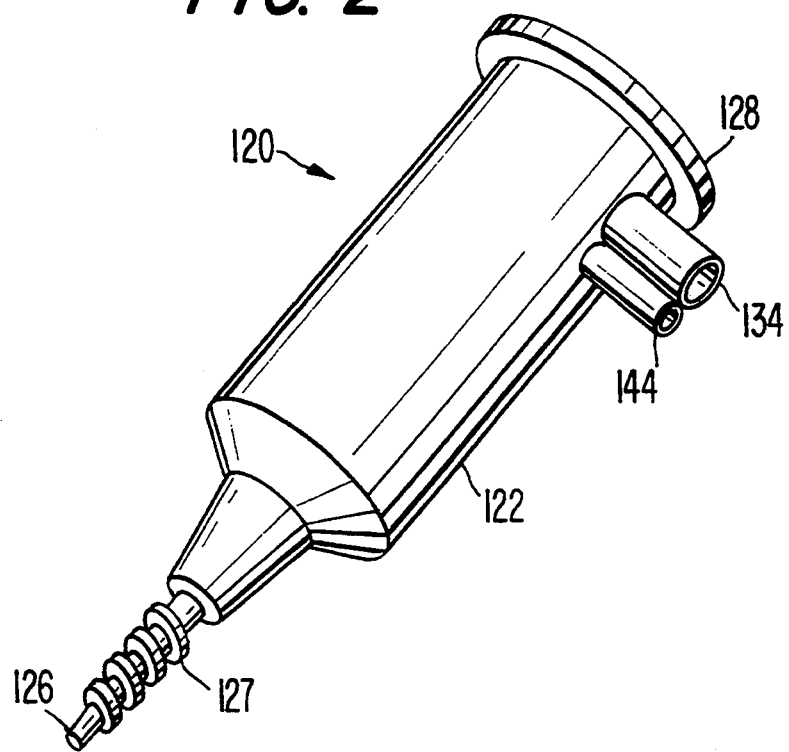
FIG. 2 is a perspective view of an empty syringe barrel used in producing a delivery apparatus according to a second embodiment of the present invention.

Referring to the embodiment of the present invention shown in FIG. 1, a container member 20 in the form of an empty syringe barrel 22 has an open end 28 and an opposite delivery or nozzle end 26. As used herein, the terms "barrel" and "container portion" encompass both cylindrical and non-cylindrical syringe bodies, and the cylindrical shape shown is for exemplary purposes only. The syringe barrel 22 is open at both ends and has a side port 24 which extends from outside the barrel 22 through the barrel wall and into the interior of the barrel 22. While the port 24 will be referred to as a side port, it will be recognized that such designation is for clarity and consistency only and does not limit the location of the port. The delivery end 26 is adapted to be sealed by appropriate means, e.g. by a tip seal 36, and the open end 28 is adapted to receive a piston 32 in a sealing manner. The side port 24 is located adjacent the delivery end in the embodiment of FIG. 1, but those skilled in the art will recognize that such location is exemplary and that the side port 24 can be disposed at various positions, e.g. between the location shown in FIG. 1 and the delivery end 26, or near the opposite end 128 of the barrel 122 as shown in the embodiment of FIG. 2. The interior of the barrel 22 serves as a container with a storage volume for holding a desired quantity of fluid material. As used herein, fluid material means a medical fluid and encompasses liquids, gases or combinations thereof, comprising or containing pharmaceutical media. As a non-limiting example, such fluid could be a contrast medium.

In the preferred embodiment, the barrel 22 is produced by a suitable plastic-forming process such as injection molding of a suitable polymer such as polypropylene, or a co-polymer of polypropylene and polyethylene. The tip seal 36 and piston can likewise be produced by injection molding a suitable elastomeric plastic or rubber material to the desired shape. In the embodiment of FIG. 3, the piston 32 is driven by a push rod 38 having a threaded protuberance 40 which engages a complimentarily threaded recess 42 formed in the piston 32. The delivery end 26 of the embodiment shown in FIG. 3 is provided with a sleeve or shroud member 46 which facilitates connection to additional medical apparatus such as, but not limited to, the luer connector of a conventional catheter (not shown).

The process of producing prefilled, sterile delivery apparatus according to one embodiment of the present invention will now be described. The syringe parts, i.e. the barrel 22, the piston 32 and the tip seal 36, are subjected to appropriate steps to wash the same and to remove any debris and contaminants as disclosed in U.S. Pat. Nos. 4,628,969 and 4,718,463, assigned to the same assignee as the present application, the subject matter of which patents is incorporated herein by reference. As disclosed in the referenced patents, the barrel 22 goes through a washing and depyrogenation step in which the barrel 22 may be inverted and subjected to a multiplicity of successive high velocity water jet washings. The tip seals 36 and pistons 32 are also subjected to a washing step to remove debris and contaminants therefrom. After washing, lubricant(s) may be an added improvement to the barrel, tip seals and pistons for ease in use, a suitable lubricant being silicon or tetrafluoroethylene. The next step in the prior art process is to assemble the tip seal 36 onto the syringe delivery end 26 and to then fill the syringe barrel 22 with a desired quantity of medical fluid. The piston 32 is then assembled in the open end 28 of the syringe barrel 22 to seal the fluid therein. The assembly of the piston 32 in the barrel 22 includes the evacuation of air from the barrel by a vacuum system to provide a selected amount of inert gas above the level of the liquid contents 30. The assembled and sealed syringe is then subjected to a sterilization process, e.g. autoclaving the syringe while maintaining a pressure on the outside of the barrel at least equal to the pressure of the contents of the barrel during the autoclaving, as disclosed in the aforementioned patents.

As stated above, improper placement of the tip seal 36 and the piston 32 causes various problems. Such problems include inadequate sealing of the fluid 30 within the barrel 22 and, particularly, bridging of the fluid past the lowermost surface of the piston 32. Referring to the embodiment shown in FIG. 3, the piston 32 has seal rings 132 with indentations 232 disposed between adjacent seal rings. The aforementioned problem of bridging occurs when, e.g. as a result of improper piston placement, fluid 30 becomes disposed in the indentations 232. This condition results in the assembled and filled syringe being discarded as the fluid within indentations 232 can facilitate the entry of contaminants into the sterile syringe contents. It would be highly preferable to avoid discarding the delivery apparatus after expending considerable time and money in assembling, filling, sealing and sterilizing the syringes.

Furthermore, such improper piston sealing can cause fluid to be sprayed from the barrel 22 onto the machinery used to assemble and fill the delivery apparatus, wasting fluid and possibly damaging the machinery. Improper placement of the piston 32 in the fluid-filled barrel 22 can also create problems when the assembled and sealed syringes are subjected to a sterilization process, e.g. being heated in an autoclave, in that movement of the piston due to thermal expansion of the fluid and/or piston may result in improper piston placement causing or aggravating the aforementioned bridging.

Accordingly, in the embodiment of the present invention as shown in FIG. 1, the delivery end 26 of an empty syringe barrel 22 is sealed by a tip seal 36, or alternatively the delivery end 26 is manufactured so as to be sealed, and the piston 32 is assembled in the open end 28 of the unfilled barrel 22 to seal the same. The proper positioning of the tip seal 36 and the piston 32 prior to filling provides a syringe barrel 22 which is sealed at both ends and is open only at the side port 24. It is possible at this time to inspect proper placement of tip seal 36 and piston 32 before filling the barrel with fluid material 30. If the apparatus does not meet the appropriate quality control standards, it is possible to discard it before it contains costly medical fluid. Additionally, it is not necessary to exercise the same amount of caution in handling the empty syringe barrel 22 while positioning the piston 32 as that required in positioning the piston in syringe barrels filled with a fluid material as disclosed in the prior art process.

Next, a desired quantity of medical fluid material 30, e.g. a contrast medium, is inserted into the barrel 22 through the side port 24. It is necessary to vent the air present in the barrel 22 while performing the filling step, and such venting can also be accomplished through the side port 24, e.g. by utilizing a filling funnel (not shown) sized so as not to completely occlude the port 24, thus leaving a portion of the port 24 through which air can escape from the barrel interior during filling. After the filling step, the side port 24 is occluded to completely seal the fluid material 30 within the barrel 22. An example of means for sealing the side port 24 is shown in the embodiment of FIG. 3 and is in the form of a resilient plug 34 press-fitted into the port 24. The filled, assembled and sealed syringe 20 is then subjected to a sterilization process, e.g. the autoclaving process disclosed in the aforementioned patents, to provide a sterile syringe with sterile contents. A requirement of the means used for sealing the side port 24 is that it be capable of withstanding such sterilization techniques without compromise of the sealed condition of the port 24.

As also discussed in the aforementioned patents, the assembled, filled and sealed syringes pass by a reject mechanism which discards those syringe barrels without a tip cap, or a piston, and/or are otherwise improperly positioned or are not ready for the next step. In contrast, in the process of the present invention both ends of the barrel are sealed prior to filling through the side port, thus it is possible to inspect the placement of the tip seal and the piston within the barrel prior to the barrel being filled with the desired fluid. This feature of the present invention is cost effective as it decreases the amount of medical fluid that is discarded as a result of faulty positioning of the tip seal and/or piston.

With reference to FIGS. 2 and 4, another embodiment of the present invention is shown and includes a hollow member 120 in the form of a empty syringe barrel 122 having an open delivery end 126 and an open opposite end 128. The delivery end 126 of this embodiment includes threads 127 optionally configured for the attachment of various medical apparatus such as by means of a complimentarily threaded nut member 124, as shown in FIG. 4, designed for securement to a conventional luer connector of a catheter (not shown). The side port of this embodiment includes two tubes 134 and 144 joined in side-by-side fashion. The larger tube 134 facilitates the injection of fluid material into the syringe barrel 122 while the tube 144 facilitates venting of air from the interior of barrel 122 during such filling.

The embodiment of FIG. 2 is shown filled and sealed in FIG. 4. The fluid material 30 is contained in the barrel 122 and the open end 128 of the barrel is sealed by a piston 33, which is provided with a backer plate 43 designed for being gripped and driven by a conventional power injection device (not shown), and the delivery end 126 is sealed by a tip seal 136. The side port is closed and sealed after filling of the barrel 122 by appropriate means, e.g. by breaking the tubes 134 and 144, which are preferably joined together by a common side wall but optionally can be separate members, from the barrel 122 at a weakened section and then occluding the remaining opening with a resilient plug 154 in a manner similar to that discussed with reference to the embodiment of FIGS. 1 and 3 or, by an other suitable means, e.g., by trimming and then crimping and/or heat sealing the tubes 134 and 144, or by simply crimping and/or heat sealing the tubes 134 and 144.

The process of the present invention thus provides an improved method of manufacturing prefilled, sterile delivery apparatus such as syringes in which it is possible to overcome the losses associated with improper sealing of the syringes, in particular, faulty piston sealing.

While the present invention and the embodiments presented herein have been set forth and described in detail for the purposes of making a full and complete disclosure of the subject matter thereof, the disclosure herein presented is not intended to be limiting in any way with respect to the true scope of this invention as the same is set forth in the appended claims.

What is claimed is:

1. A method of producing a prefilled, sterile delivery device having a container portion with a sealed tip end and an opposite open end, and a piston positioned within said open end and slidable in sealing engagement with the container portion to retain a fluid therein; the method comprising the steps of:

forming a container portion with a sealed tip at one end, an open opposite end adapted to receive a piston, and a port disposed between the sealed tip end and the open opposite end through which the container portion can be filled with a desired quantity of fluid material;

removing debris and other contaminants from the piston;

removing debris from the container portion;

assembling the piston in the open end of the container portion so that the piston is disposed at a position between the port and the open end of the container portion;

filling the container portion through the port with the desired quantity of fluid material while the piston remains in said position within the container portion;

closing and sealing said port after said filling step to provide a sealed container portion with the fluid material sealed therein between the piston and the sealed tip of the container portion; and sterilizing the assembled and sealed delivery device to provide a sterile delivery device with sterile fluid contents.

2. A method as claimed in claim 1, wherein the step of forming a container portion with a sealed tip end comprises attaching a tip seal separate from the container portion to said one end of the container portion.

3. A method as claimed in claim 1, wherein the filling step comprises filling the container portion with a medical fluid.

4. A method as claimed in claim 1, wherein the sterilizing step comprises autoclaving the assembled and sealed delivery apparatus.

5. A method as claimed in claim 1, wherein the step of forming a container portion comprises forming a molded plastic barrel.

6. A method as claimed in claim 5, wherein the sterilizing step comprises autoclaving the assembled and sealed delivery apparatus.

7. A method as claimed in claim 6, wherein the autoclaving step is performed by heating the assembled and sealed delivery apparatus to a temperature in the range of 120° to 125° C.

8. A method as claimed in claim 6, wherein the autoclaving step is performed while maintaining a pressure on the outside of the container portion which is at least equal to the pressure of the contents of the container portion during the autoclaving.

9. A method as claimed in claim 6, wherein the step of forming a container portion with a sealed tip end comprises attaching a tip seal separate from the container portion to said one end of the container portion.

10. A method of producing a prefilled sterile delivery device having sterile contents, the method comprising steps of:

a) forming a container having a sealed nozzle end, an open opposite end, and a filling port disposed in the container between said sealed nozzle end and said open opposite end;

b) positioning a piston into the open opposite end of said container so as to be located in a position between the filling port and the open opposite end, wherein the piston seals said open opposite end and is slidable therein, the container defining a sealed storage volume between said sealed nozzle end and said piston;

c) inspecting the position of said piston in said open opposite end of the container to insure that the piston will properly seal medical fluid contained in said storage volume;

d) filling the container through said filling port with medical fluid while the piston remains in said position in the open opposite end of the container until said storage volume contains a desired amount of the fluid;

e) closing and sealing said filling port to sealingly enclose the medical fluid within said storage volume between the piston and the sealed tip of the container portion; and f) sterilizing the filled, sealed container to provide a prefilled sterile delivery device containing sterile medical fluid therein.

11. A method according to claim 10, wherein the filled, sealed container is sterilized by autoclaving.

12. A method according to claim 10, wherein the sealed nozzle end of said container is formed by attaching a tip seal separate from the container to the nozzle end of said container.

* * * * *

UNITED STATES PATENT AND TRADEMARK OFFICE
CERTIFICATE OF CORRECTION

PATENT NO. : 5,373,684
DATED : December 20, 1994
INVENTOR(S) : Rita D. Vacca

It is certified that error appears in the above-indentified patent and that said Letters Patent is hereby corrected as shown below:

Title page, item [54] and col. 1, in the Title should be replace with -- PROCESS USED IN PRODUCING PREFILLED, STERILE APPARATUS --.

Signed and Sealed this

Eleventh Day of July, 1995

*Attest:*

BRUCE LEHMAN

*Attesting Officer*     *Commissioner of Patents and Trademarks*